United States Patent
Okuno (10) Patent No.: US 9,364,188 B2
(45) Date of Patent: Jun. 14, 2016

(54) X-RAY APPARATUS FOR ROUND VISIT

(75) Inventor: Tomoharu Okuno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 121 days.

(21) Appl. No.: 14/367,150

(22) PCT Filed: Dec. 22, 2011

(86) PCT No.: PCT/JP2011/007223
§ 371 (c)(1),
(2), (4) Date: Jun. 19, 2014

(87) PCT Pub. No.: WO2013/093984
PCT Pub. Date: Jun. 27, 2013

(65) Prior Publication Data
US 2014/0369477 A1    Dec. 18, 2014

(51) Int. Cl.
*A61B 6/00* (2006.01)
*A61B 6/10* (2006.01)

(52) U.S. Cl.
CPC ............. *A61B 6/4405* (2013.01); *A61B 6/105* (2013.01); *A61B 6/54* (2013.01); *A61B 6/547* (2013.01)

(58) Field of Classification Search
CPC ........ A61B 6/105; A61B 6/4405; A61B 6/54; A61B 6/547
See application file for complete search history.

(56) References Cited

U.S. PATENT DOCUMENTS

| | | | |
|---|---|---|---|
| 4,336,858 A * | 6/1982 | Loyzim | A61B 6/00 180/179 |
| 5,764,009 A | 6/1998 | Fukaya et al. | |
| 2006/0126795 A1 * | 6/2006 | Lumma | A61B 6/4464 378/193 |
| 2008/0048597 A1 | 2/2008 | Tamaoka | |
| 2010/0171452 A1 | 7/2010 | Fukushima | |
| 2012/0093294 A1 * | 4/2012 | Lalena | A61B 6/4266 378/98.2 |

FOREIGN PATENT DOCUMENTS

| | | |
|---|---|---|
| JP | 8-65809 A | 3/1996 |
| JP | 2000-201914 A | 7/2000 |
| JP | 2001-097221 A | 4/2001 |
| JP | 2005-059776 A | 3/2005 |
| JP | 2008-22678 A | 1/2008 |
| JP | 2010-187820 A | 9/2010 |
| WO | 2009/110321 A1 | 9/2009 |

OTHER PUBLICATIONS

Notification of Reasons for Refusal JP 2013-549964 dated Dec. 24, 2014.
International Search Report PCT/JP2011/007223 dated Jan. 31, 2012.

* cited by examiner

*Primary Examiner* — Glen Kao
(74) *Attorney, Agent, or Firm* — McDermott Will & Emery LLP (57) ABSTRACT

With an X-ray apparatus for round visit of this invention, when a brake operation is carried out, a CPU performs deceleration control (braking current control at c and short brake control at e) of a movable carriage instead of immediately driving electromagnetic brakes, and drives the electromagnetic brakes at time f. Therefore, a great shock does not occur to the apparatus, and there is no possibility of the operator colliding with the apparatus. Since the deceleration control of the movable carriage is carried out in advance, the apparatus does not stop suddenly and does not impair the floor. As a result, the X-ray apparatus for round visit is realized, in which no great shock occurs to the apparatus at times of deceleration, and which is also safe for the operator.

12 Claims, 5 Drawing Sheets

X-RAY APPARATUS FOR ROUND VISIT

CROSS REFERENCE TO RELATED APPLICATIONS

This application is a U.S. National Stage application under 35 U.S.C. §371, of International Application PCT/JP2011/007223 filed on Dec. 22, 2011, which was published as WO 2013/093984 on Jun. 27, 2013. The application is incorporated herein by reference.

TECHNICAL FIELD

This invention relates to an X-ray apparatus for round visit having an X-ray emitting device, a movable carriage and so on, and more particularly to deceleration control of the movable carriage.

BACKGROUND ART

Conventionally, the X-ray apparatus for round visit, since this apparatus is 400kg or more in weight, has traveling motors. The X-ray apparatus for round visit is movable driven by the motors. By operating to and fro a lever handle provided for the apparatus, the motors can rotate to cause forward and backward movements. When it is desired to slow down such X-ray apparatus for round visit, the motors are placed in a deceleration state by returning the lever handle to a center position. Such apparatus includes a bridge circuit (see FIG. 4), and driving and deceleration control of the motors can be carried out by ON/OFF control of switching elements Q1-Q4 of the bridge circuit (see Patent Document 1, for example).

Incidentally, a brake lever is attached to the lever handle in order to stop the apparatus completely. When the brake lever is released, brake lever input is inputted to a CPU. Electromagnetic brakes are attached to traveling drive wheels, and the CPU outputs a brake drive command to the electromagnetic brakes in response to the above brake lever input. Consequently, the traveling drive wheels connected to the motors are completely locked by the electromagnetic brakes, whereby the apparatus can stop even in a sloping position. Therefore, in order to cause the apparatus to travel, the operator first grips the brake lever and displaces the lever handle in a traveling direction (forward or backward), and when stopping the apparatus, returns the lever handle to the center position, and releases the brake lever.

PRIOR ART DOCUMENT

Patent Document

[Patent Document 1]
Unexamined Patent Publication No. 2010-187820

SUMMARY OF INVENTION

Technical Problem

However, when the operator releases the brake lever to stop the apparatus, and if the brake lever is released in a high-speed state (at 5 km/h in normal traveling) the apparatus, the electromagnetic brakes will act immediately to lock the traveling drive wheels. Since the apparatus comes to a sudden stop at this time, a large decelerating force will be applied to the apparatus, and a great shock will occur to the apparatus, causing vibration. Since the operator is moving like the apparatus, when the apparatus first makes a sudden stop, the operator may also collide with the apparatus, and thus it is also dangerous for the operator. Further, strong friction can be produced between the traveling drive wheels and the floor, and there is a possibility of impairing the floor.

This invention has been made having regard to the state of the art noted above, and its object is to provide an X-ray apparatus for round visit, which apparatus is not subjected to a great shock in time of deceleration, and is safe also for the operator.

Solution to Problem

To fulfill the above object, this invention provides the following construction.

An X-ray apparatus for round visit of this invention comprises an X-ray emitting device for emitting X-rays; a movable carriage having the X-ray emitting device; traveling drive wheels for moving the movable carriage; motors for driving the traveling drive wheels; and brakes for stopping the movable carriage; the X-ray apparatus for round visit further comprising a deceleration control device for carrying out deceleration control of the movable carriage before driving the brakes when a brake operation is carried out for operating the brakes.

According to the X-ray apparatus for round visit of this invention, when a brake operation is carried out, the deceleration control device performs deceleration control of the movable carriage instead of immediately driving the brakes. Therefore, a great shock does not occur to the apparatus, and there is no possibility of the operator colliding with the apparatus. Since the deceleration control of the movable carriage is carried out in advance, the apparatus does not stop suddenly and does not impair the floor. As a result, the X-ray apparatus for round visit is realized, in which no great shock occurs to the apparatus at times of deceleration, and which is also safe for the operator.

One example of the above X-ray apparatus for round visit of this invention comprises a driving circuit having switching elements, wherein the deceleration control device carries out the deceleration control by driving the switching elements to short-circuit the driving circuit and apply short brakes. With this example, after the short brakes, the brakes are driven to attain a completely stopped state. This realizes a smooth deceleration before the apparatus stops.

With the above example (the former), sufficient deceleration may not be obtained from the deceleration by the short brakes. To deal with such a case, another example (the latter) of the above X-ray apparatus for round visit of this invention comprises a driving circuit having switching elements, wherein the deceleration control device carries out the deceleration control by driving the switching elements to feed a motor drive current in an opposite direction to a direction of rotation of the motors at a time of traveling drive. With this example, after the deceleration control which feeds the motor drive current in the opposite direction to the direction of rotation of the motors at the time of traveling drive, the brakes are driven to attain a completely stopped state. Strong torque occurs to the motors by feeding the motor drive current in the opposite direction to the direction of rotation of the motors at the time of traveling drive, to place the motors in a strong deceleration state. This realizes smooth deceleration before the apparatus stops.

The former and the latter may be combined.

That is, it is possible to carry out continuously a short brake control (the former) as the deceleration control by driving the switching elements to short-circuit the driving circuit and apply short brakes, and a braking current control (the latter) as the deceleration control by driving the switching elements to feed a motor drive current in an opposite direction to a direction of rotation of the motors at a time of traveling drive. For example, when traveling at a relatively high speed, strong deceleration may be carried out using the latter, braking current control. When the speed has fallen to some level, deceleration may be carried out using the former, short brakes. It is therefore preferable to carry out the short brake control after the braking current control.

For the braking current control (the latter), it is preferred that the apparatus comprises a pulse generating device for generating pulses, and carrying out ON/OFF control of the switching elements by supplying the pulses to the switching elements; and a duty ratio altering device for altering duty ratios which are pulse widths divided by pulse periods of the pulses generated by the pulse generating device; wherein the deceleration control device carries out the deceleration control through the ON/OFF control of the switching elements, while the duty ratio altering device alters the duty ratios. A still smoother deceleration is realized by carrying out the deceleration control while altering the duty ratios.

It is particularly preferred that the apparatus comprises a rotating speed detecting device for detecting rotating speeds of the motors; wherein the duty ratio altering device alters the duty ratios by determining pulse widths proportional to the rotating speeds of the motors detected by the rotating speed detecting device. Since the pulse widths, and thus the duty ratios, are altered in proportion to the rotating speeds of the motors detected by the rotating speed detecting device, a still smoother deceleration is realized. For example, the pulse widths are determined from $W=\alpha \times R/Rmax$, where W represents the pulse widths, a represents a deceleration constant, R represents the rotating speeds of the motors, and Rmax represents a maximum rotating speed of the motors.

Advantageous Effects of Invention

With the X-ray apparatus for round visit according to this invention, when a brake operation is carried out, the deceleration control device performs deceleration control of the movable carriage instead of immediately driving the brakes. Therefore, a great shock does not occur to the apparatus, and there is no possibility of the operator colliding with the apparatus. Since the deceleration control of the movable carriage is carried out in advance, the apparatus does not stop suddenly and does not impair the floor.

DESCRIPTION OF EMBODIMENTS

Figure 1:
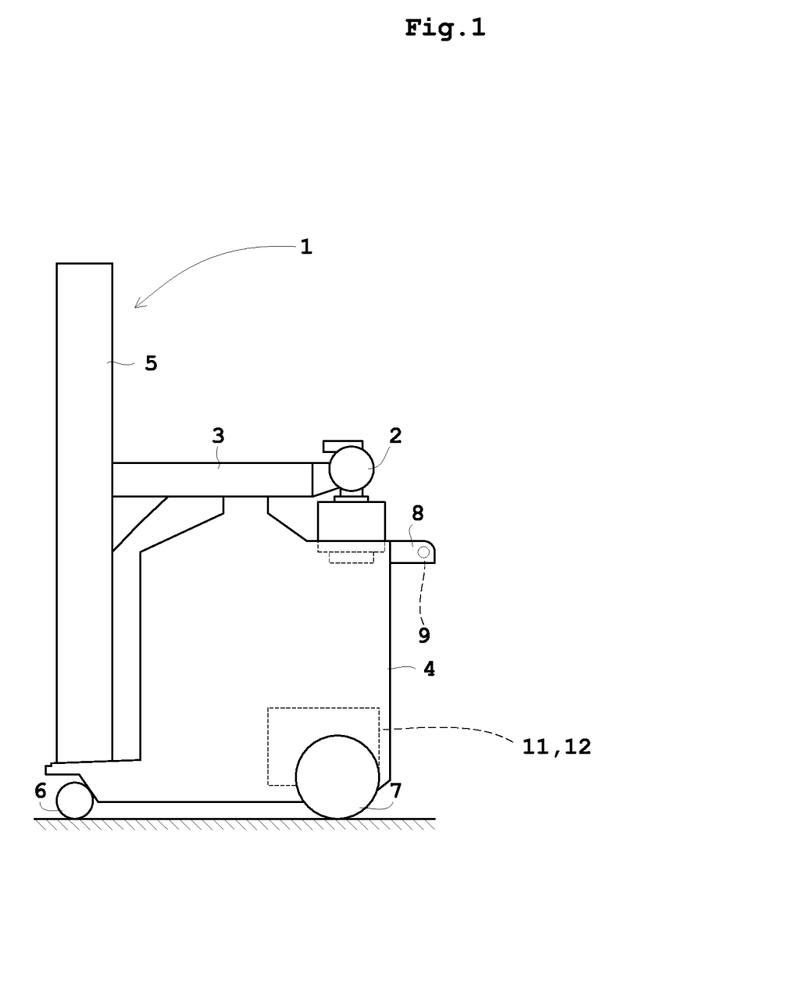
FIG. 1 is a schematic side view of an X-ray apparatus for round visit according to an embodiment.
Figure 2:
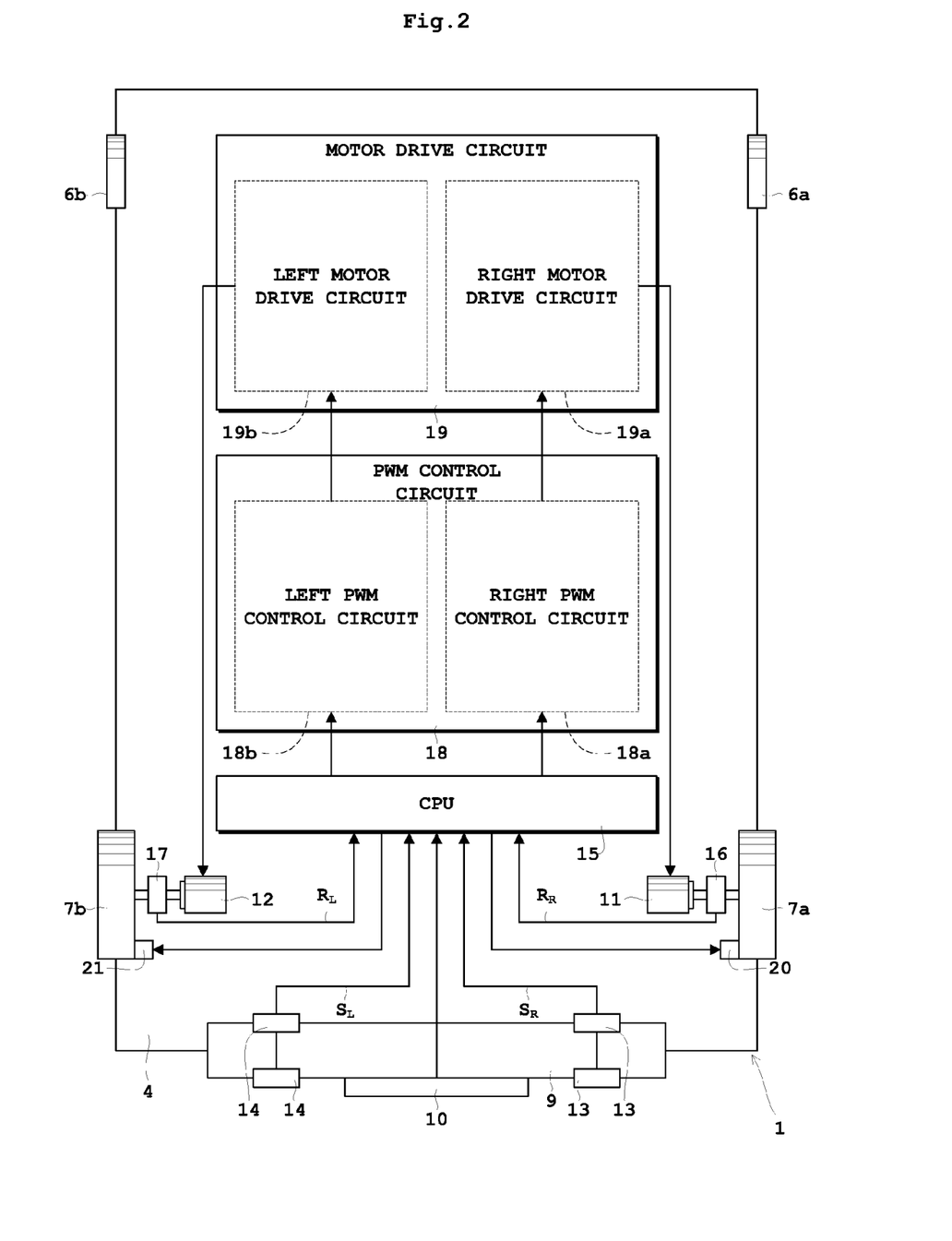
FIG. 2 is a block diagram showing the construction of the X-ray apparatus for round visit according to the embodiment.
Figure 3:
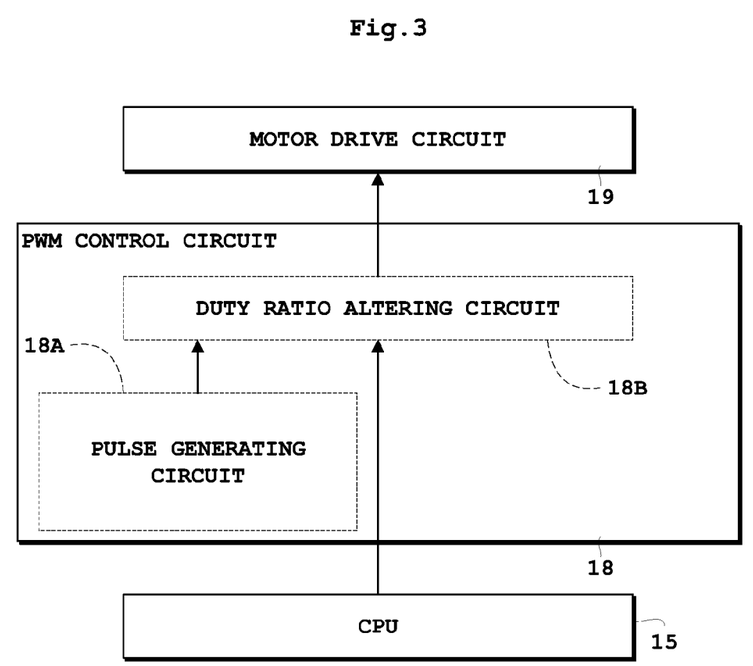
FIG. 3 is a block diagram showing a PWM control circuit and adjacent components according to the embodiment.
Figure 4:
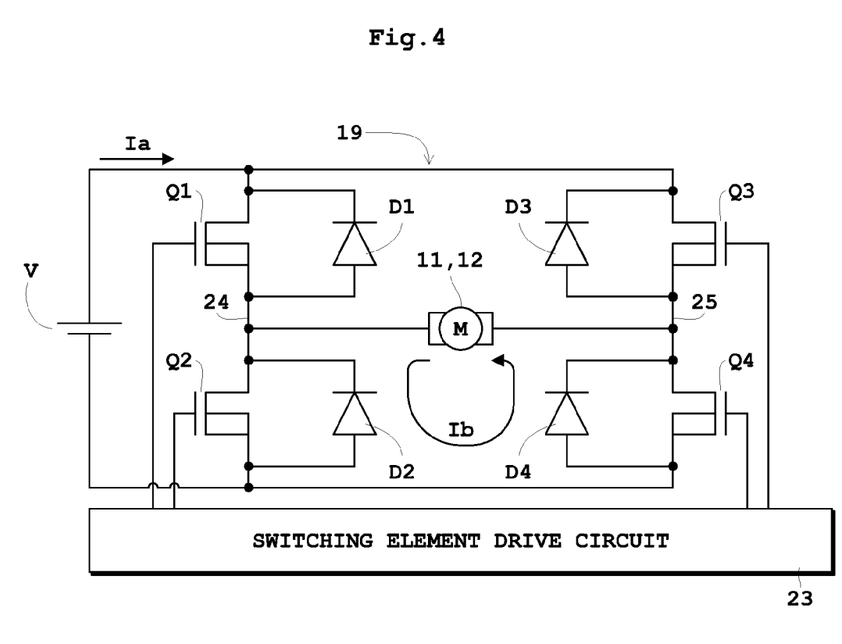
FIG. 4 is a circuit diagram showing a motor drive circuit according to the embodiment.

An embodiment of this invention will be described hereinafter with reference to the drawings. FIG. 1 is a schematic side view of an X-ray apparatus for round visit according to an embodiment. FIG. 2 is a block diagram showing the construction of the X-ray apparatus for round visit according to the embodiment. FIG. 3 is a block diagram showing a PWM control circuit and adjacent components according to the embodiment. FIG. 4 is a circuit diagram showing a motor drive circuit according to the embodiment.

As shown in FIG. 1, an X-ray apparatus for round visit 1 includes an X-ray tube 2 for emitting X-rays, an arm 3 for holding the X-ray tube 2, a movable carriage 4 (see FIG. 2 also) having the X-ray tube 2 and arm 3, a strut 5 swivelable on the movable carriage 4 while supporting the arm 3, front wheels 6 arranged in bottom forward positions of the movable carriage 4, and rear wheels 7 arranged in bottom rearward positions of the movable carriage 4. The X-ray tube 2 corresponds to the X-ray emitting device in this invention. The movable carriage 4 corresponds to the movable carriage in this invention. The rear wheels 7 correspond to the traveling drive wheels in this invention.

The arm 3 is horizontally extendible and contractible, and is constructed vertically movable relative to the strut 5. The strut 5 is swiveled on the movable carriage 4 to swivel the X-ray tube 2 with the arm 3 supported by the strut 5. Particularly when X-raying is carried out with a bed attached forward in a traveling direction of the movable carriage 4, the X-ray tube 2 is swiveled with the arm 3 through 180° in a level plane from the state of FIG. 1. When X-raying is carried out with a bed attached laterally with respect to the traveling direction of the movable carriage 4, the X-ray tube 2 is swiveled with the arm 3 through 90° in a level plane from the state of FIG. 1.

In addition, the X-ray apparatus for round visit 1 includes a handle holding rack 8 formed at the rear of the movable carriage 4, a lever handle 9 (see FIG. 2 also) held by the handle holding rack 8, and a brake lever 10 (see FIG. 2) attached to the rear of the lever handle 9. In addition, as shown in FIG. 2, the X-ray apparatus for round visit 1 includes a right motor 11 and a left motor 12 (see FIG. 1 also) for driving the rear wheels 7 (right rear wheel 7a and left rear wheel 7b), respectively, a right pressure sensor 13 and a left pressure sensor 14 for detecting directions of displacement and amounts of displacement of the lever handle 9, respectively, a CPU 15 for performing drive control and deceleration control of the movable carriage 4, a right encoder 16 and a left encoder 17 for detecting rotating speeds R of the right motor 11 and the left motor 12, respectively, a PWM control circuit 18 for performing pulse width modulation control (hereinafter abbreviated as "PWM control"), a motor drive circuit 19 consisting of a bridge circuit with switching elements Q1-Q4 (see FIG. 4), a right electromagnetic brake 20 and a left electromagnetic brake 21 provided respectively for the right rear wheel 7a and left rear wheel 7b for stopping the movable carriage 4. The right motor 11 and left motor 12 correspond to the motors in this invention. The CPU 15 corresponds to the deceleration control device in this invention. The right encoder 16 and left encoder 17 correspond to the rotating speed detecting device in this invention. The motor drive circuit 19 corresponds to the driving circuit in this invention. The right electromagnetic brake 20 and left electromagnetic brake 21 correspond to the brakes in this invention.

The front wheels 6 (see FIG. 1) form a right and left pair seen in the traveling direction of the movable carriage 4, and also the rear wheels 7 (see FIG. 1) form a right and left pair seen in the traveling direction of the movable carriage 4. That is, the front wheels 6 consist of a right front wheel 6a and a left front wheel 6b, and the rear wheels 7 consist of a right rear wheel 7a and a left rear wheel 7b. The right motor 11 is attached to an axle of the right rear wheel 7a, and the left motor 12 is attached to an axle of the left rear wheel 7b. With the right motor 11 driving the right rear wheel 7a and the left motor 12 driving the left rear wheel 7b, the rear wheels 7 move the movable carriage 4. The front wheels 6 consist of swivelable casters, the front wheels 6 being freely movable with movement of the movable carriage 4.

The front wheels 6 and rear wheels 7 have rubber tires or the like used thereon, to be designed to move freely into and out of patients' rooms, operating rooms and elevators, and besides have a braking system, a cassette box and accessory equipment. It is important for this X-ray apparatus for round visit 1 to be small and lightweight and have good traveling operability as a mobile apparatus, which easily moves to the bedrooms, artificial rooms, operating rooms, children's rooms, X-ray rooms, infants' rooms and so on in a hospital, to be readily used for X-raying on site.

The lever handle 9 is connected to the movable carriage 4 through relatively hard but flexible spring members. The two spring members connected to opposite sides of the movable carriage 4 are in form of hard blade springs. With the spring members provided, the lever handle 9 can be displaced slightly forward and backward in response to forces applied to the lever handle 9 to push and pull the lever handle 9. By operating the lever handle 9 forward and backward, the lever handle 9 can be displaced relatively easily by spring action of the spring members, and when released, the lever handle 9 can return to neutral position or center position quickly.

A pair of linear magnets are attached to opposite ends of the lever handle 9, respectively, to be movable with the lever handle 9. On the other hand, a pair of hall effect sensors (right pressure sensor 13 and left pressure sensor 14) are attached to the movable carriage 4, as arranged adjacent the corresponding magnets, respectively.

When the hall effect sensors (right pressure sensor 13 and left pressure sensor 14) are in center positions relative to the magnets, output signals of the hall effect sensors (right pressure sensor 13 and left pressure sensor 14) are zero level. When the magnets are shifted, the output signals of the hall effect sensors (right pressure sensor 13 and left pressure sensor 14) will change substantially linearly between positive maximum and negative maximum.

Signs (that is, polarities) of the output signals of the hall effect sensors indicate directions of displacement of the lever handle 9, and the amplitude of the output signals is proportional to displacement. Thus, operational forces applied to the lever handle 9 can be converted to electric signals (operational force signals: output signals of the hall effect sensors). The operational forces may be detected using pressure sensors other than the hall sensors.

When the operator operates the lever handle 9 of the movable carriage 4 forward and backward, the right pressure sensor 13 and left pressure sensor 14, operational force signals (right operational force signal $S_R$ and left operational force signal $S_L$) from the right pressure sensor 13 and left pressure sensor 14 arranged at the opposite ends of the lever handle 9 are independently inputted to the CPU 15. On the other hand, from the right encoder 16 and left encoder 17 attached to the axles of the right rear wheel 7a and left rear wheel 7b for detecting rotating speeds R of the right motor 11 and the left motor 12 (right rotating speed $R_R$ and left rotating speed $R_L$), respectively, conversion is made into electric signals (motor rotating speed signals). And the motor rotating speed signals are inputted to the CPU 15.

Next, the CPU 15 calculates, independently of each other, pulse widths proportional to the rotating speeds R of the right motor 11 and the left motor 12 (right rotating speed $R_R$ and left rotating speed $R_L$) detected by the right encoder 16 and left encoder 17, and sends them to a duty ratio altering circuit 18B (see FIG. 3) of the PWM control circuit 18. The duty ratio altering circuit 18B alters duty ratios by determining the pulse widths sent. By sending switching pulse signals, based on these duty ratios, to the motor drive circuit 19 independently of each other, the CPU 15 performs deceleration control by ON/OFF controlling of the switching elements Q1-Q4 (see FIG. 4), while altering the duty ratios in the duty ratio altering circuit 18B.

The right motor 11 and left motor 12 are individually controlled by the motor drive circuit 19. The motor drive circuit 19 consists of a right motor drive circuit 19a and a left motor drive circuit 19b, both having the same circuit configuration. The right motor drive circuit 19a controls rotation of the right motor 11, and the left motor drive circuit 19b controls rotation of the left motor 12.

The motor drive circuit 19 undergoes the PWM control by the PWM control circuit 18. The PWM control circuit 18 also consists of a right PWM control circuit 18a and a left PWM control circuit 18b, both being the same control circuits. The right PWM control circuit 18a sends a switching pulse signal to the right motor drive circuit 19a, and the left PWM control circuit 18b sends a switching pulse signal to the left motor drive circuit 19b. The switching pulse signals have the duty ratios altered in the duty ratio altering circuit 18B (see FIG. 3) of the PWM control circuit 18.

The right electromagnetic brake 20 and left electromagnetic brake 21 are provided for the right rear wheel 7a and left rear wheel 7b, respectively. The right electromagnetic brake 20 and left electromagnetic brake 21 are both the same electromagnetic brakes, and are formed of disk brakes in this embodiment. When the operator releases the brake lever 10, a brake lever input is inputted to the CPU 15. In response to the above brake lever input, the CPU 15 outputs a brake drive command to the right electromagnetic brake 20 and left electromagnetic brake 21, respectively. Consequently, the right rear wheel 7a connected to the right motor 11 is completely locked by the right electromagnetic brake 20, and the left rear wheel 7b connected to the left motor 12 is completely locked by the left electromagnetic brake 21, thereby stop-ping the movable carriage 4.

The PWM control circuit 18, as shown in FIG. 3, includes a pulse generating circuit 18A for generating pulses (switching pulse signals) and performing ON/OFF control of the switching elements Q1-Q4 by feeding the pulses to the switching elements Q1-Q4 (see FIG. 4), and the duty ratio altering circuit 18B for altering the duty ratios which are pulse widths divided by pulse periods of the pulses generated by the pulse generating circuit 18A. The switching pulse signals with the duty ratios altered by the duty ratio altering circuit 18B are sent to the motor drive circuit 19. The pulse generating circuit 18A corresponds to the pulse generating device in this invention. The duty ratio altering circuit 18B corresponds to the duty ratio altering device.

And the duty ratio altering circuit 18B alters the duty ratios by determining pulse widths proportional to the rotating speeds R (right rotating speed $R_R$ and left rotating speed $R_L$) of the right motor 11 and left motor 12 detected by the right encoder 16 and left encoder 17. The alteration of the duty ratios by the duty ratio altering circuit 18B will be described in detail hereinafter.

The motor drive circuit 19, as shown in FIG. 4, includes a DC power source V which outputs DC constant voltage, drive motors (right motor 11 and left motor 12) for causing the apparatus to travel by the current supplied, H bridge circuits formed of switching elements Q1-Q4 such as FET transistors, diodes D1-D4 connected in parallel to the respective switching elements Q1-Q4, and a switching element drive circuit 23 for turning the switching elements Q1-Q4 ON and OFF.

Q1 and Q2 are connected in series to a feeder wire 24 connected at opposite ends thereof to the DC power source V. Q3 and Q4 are connected in series to a feeder wire 25 connected at opposite ends thereof to the DC power source V. That is, the feeder wire 24 and feeder wire 25 are connected in parallel to each other. The drive motors (right motor 11 and left motor 12) have opposite poles connected, respectively, to the feeder wire 24 between Q1 and Q2 and to the feeder wire 25 between Q3 and Q4.

According to this bridge circuit, the drive motors (right motor 11 and left motor 12) can be driven to rotate forward when Q1 is placed in ON state, Q2 and Q3 are placed in OFF state, and Q4 is PWM-controlled. The drive motors (right motor 11 and left motor 12) can be driven to rotate backward when Q3 is placed in ON state, Q1 and Q4 are placed in OFF state, and Q2 is PWM-controlled.

When, for example, it is desired to move the X-ray apparatus for round visit 1 forward and the lever handle 9 is operated forward, the CPU 15 calculates pulse widths (or duty ratios) and sends them to the duty ratio altering circuit 18B, based on the operational force signals (right operational force signal $S_R$ and left operational force signal $S_L$) at the time from the right pressure sensor 13 and the left pressure sensor 14 from the opposite ends of the lever handle 9, and the rotating speeds R (right rotating speed $R_R$ and left rotating speed $R_L$) of the drive motors (right motor 11 and left motor 12) detected by the right encoder 16 and left encoder 17. The duty ratio altering circuit 18B, while altering the duty ratios corresponding to the current operational force signals and rotating speeds, sends switching pulse signals to the switching element drive circuit 23 of the motor drive circuit 19. The switching element drive circuit 23 emits driving signals based on these switching pulse signals to carry out the ON/OFF control of the switching elements Q1 and Q4. When the switching elements Q1 and Q4 are in ON state, a closed circuit is formed by the DC power source V, switching element Q1, drive motors (right motor 11 and left motor 12) and switching element Q4. A motor drive current Ia will flow as a result, and the drive motors (right motor 11 and left motor 12) will rotate forward to accelerate the X-ray apparatus for round visit 1 forward.

On the other hand, when it is desired to move the X-ray apparatus for round visit 1 backward and, similarly, the lever handle 9 is operated backward, the switching element drive circuit 23 emits driving signals and the switching elements Q2 and Q3 become ON state. A drive current will flow in the opposite direction to the above drive current Ia, and the drive motors (right motor 11 and left motor 12) will rotate reversely to move the X-ray apparatus for round visit 1 backward.

Next, operation at a short braking time (short brake control) will be described. When the operator returns the lever handle 9 to the neutral position during a forward traveling, for example, short brakes operate to decelerate the traveling. Assuming that the switching elements Q1 and Q4 of the motor drive circuit 19 have been in ON state for constant speed traveling up to that time, and when the short brakes operate then, the switching element drive circuit 23 places Q1, Q3 and Q4 in OFF state, with only Q2 subjected to the ON/OFF control by PWM control (in this embodiment, only ON control is carried out since the duty ratio is 100% at the time of short brake control as described hereinafter). Although the drive current Ia does not flow to the drive motors (right motor 11 and left motor 12) since Q1 and Q4 are in OFF state, a counter electromotive voltage already occurs at the opposite ends of the drive motors (right motor 11 and left motor 12). Therefore, for a period in which Q2 is in ON state, a braking current Ib flows in the opposite direction to the drive current Ia to a short circuit formed by the drive motors (right motor 11 and left motor 12), Q2 and D4 to slow down the drive motors (right motor 11 and left motor 12) (short brakes). The value of braking current Ib corresponds to the counter electromotive voltage generated at the drive motors (right motor 11 and left motor 12) divided by wirewound resistors of the drive motors (right motor 11 and left motor 12). In this way, the CPU 15 carries out deceleration control by driving the switching elements Q1-Q4 to short-circuit the motor drive circuit 19 and apply the short brakes.

Next, operation for feeding a braking current (braking current control) by a technique other than the short brake control will be described. When the operator returns the lever handle 9 to the neutral position during a forward traveling, for example, a braking current is fed without short-circuiting the motor drive circuit 19, to decelerate the traveling. Assuming that the switching elements Q1 and Q4 of the motor drive circuit 19 have been in ON state for constant speed traveling up to that time, and when the braking current control operates then, the switching element drive circuit 23 places Q1 and Q4 in OFF state, with Q2 and Q3 subjected to the ON/OFF control by PWM control. Since Q1 and Q4 are in OFF state and Q2 and Q3 in ON state, a current flows as braking current toward Q2, the drive motors (right motors 11 and left motor 12) and Q3. As a result, the braking current flows in the opposite direction to the drive current Ia to slow down the drive motors (right motor 11 and left motor 12) (braking current control). In this way, the CPU 15 carries out deceleration control by driving the switching elements Q1-Q4 to feed a motor drive current (that is, braking current) in the opposite direction to the direction of rotation of the drive motors (right motor 11 and left motor 12) at the time of traveling drive.

Figure 5:
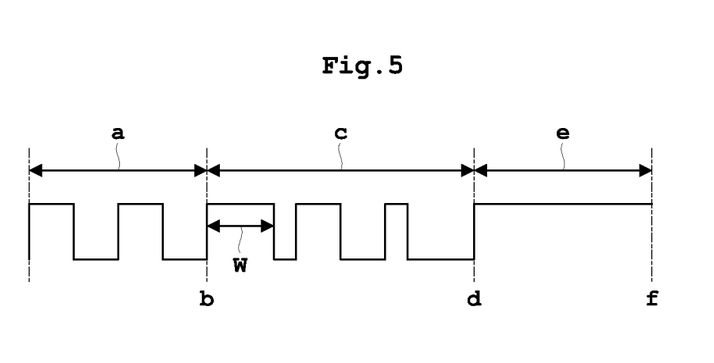
FIG. 5 is a timing chart of a switching pulse signal according to the embodiment.

Next, the deceleration control by the CPU 15 in this embodiment will be described with reference to FIG. 5. FIG. 5 is a timing chart of a switching pulse signal according to the embodiment. When a brake operation is carried out (here, the operator releases the brake lever 10) for operating the electromagnetic brakes (right electromagnetic brake 20 and left electromagnetic brake 21), the CPU 15 carries out deceleration control of the movable carriage 4 before the electromagnetic brakes (right electromagnetic brake 20 and left electromagnetic brake 21) are driven by the operator releasing the brake lever 10. That is, when the operator releases the brake lever 10, the electromagnetic brakes are not driven immediately, but the electromagnetic brakes are driven after the above short brake control or braking current control is carried out in advance. The brake operation is not limited to release of the brake lever 10 by the operator. Conversely, a brake operation may be carried out when the operator grasps the brake lever 10, or a brake operation may be carried out when a button or the like is pushed. Thus, there is no particular limitation to a specific operation for brake operation.

Generally, since torque is weaker in the short brake control than in the braking current control, the short brake control and the braking current control are combined to carry out the short brake control and braking current control continuously. More desirably, the short brake control with weak torque is carried out after the braking current control with strong torque, thereby to realize smooth deceleration.

First, as shown in FIG. 5, in a state of constant speed at about 5 km/h (see a in FIG. 5), the switching pulse signal is outputted with a constant duty ratio. When the operator releases the brake lever 10 at a time b in FIG. 5, the braking current control is performed (see c in FIG. 5).

The duty ratio at this time is calculated by determining pulse widths proportional to the rotating speeds R (right rotating speed $R_R$ and left rotating speed $R_L$) of the drive motors (right motor 11 and left motor 12). The pulse widths are determined from the following equation (1):

$$W = \alpha \times R / R\max \quad (1)$$

where, as shown in FIG. 5, W represents the pulse widths, α represents a deceleration constant, R represents the rotating speeds of the drive motors detected by the encoders, and Rmax represents a maximum rotating speed of the drive motors.

This results in a strong torque acting on the drive motors to place the drive motors in a strong deceleration state.

Subsequently, the CPU 15, when detecting the speed of the apparatus (movable carriage 4) having fallen sufficiently (eg to 1 km/h or less) (see d in FIG. 5) by detecting the rotating speeds through the encoders, carries out the short brake control (see e in FIG. 5).

The duty ratio at this time is set to 100%. Of course, it is not absolutely necessary to set it to 100%, but since, as noted hereinbefore, torque is weaker in the short brake control than in the braking current control, it is preferable to set the duty ratio to 100% to maintain the switching elements in ON state. After a predetermined time (eg about 0.5 sec.), at time f in FIG. 5, the CPU 15 outputs a brake drive command to the electromagnetic brakes to drive the electromagnetic brakes, thereby to bring about a completely stopped state.

According to the X-ray apparatus for round visit 1 in this embodiment having the construction described above, when a brake operation is carried out, the deceleration control device (CPU 15 in this embodiment) performs deceleration control of the movable carriage 4 instead of immediately driving the brakes (electromagnetic brakes in this embodiment). Therefore, a great shock does not occur to the apparatus, and there is no possibility of the operator colliding with the apparatus. Since the deceleration control of the movable carriage 4 is carried out in advance, the apparatus does not stop suddenly and does not impair the floor. As a result, the X-ray apparatus for round visit 1 is realized, in which no great shock occurs to the apparatus at times of deceleration, and which is also safe for the operator.

Conventionally, when electromagnetic brakes are made powerful in order to stop the apparatus especially in a leaning state, the electromagnetic brakes driven immediately while traveling will cause the apparatus to stop suddenly with a great shock. It is therefore necessary to take measures such as additionally providing weak electromagnetic brakes for the purpose of deceleration. In this case, space for installing the weak electromagnetic brakes in the apparatus will be needed, and will result in an increase in cost. However, in the case of this embodiment it is not necessary to provide electromagnetic brakes for the purpose of deceleration even in stopping the apparatus in a leaning state, which is an advantage of not needing to improve the conventional apparatus drastically.

In this embodiment, the deceleration control device (CPU 15 in this embodiment) carries out the deceleration control by driving the switching elements Q1-Q4 to short-circuit the driving circuit (motor drive circuit 19) and apply the short brakes. In this case, the brakes (electromagnetic brakes in this embodiment) are driven after the short brakes, to attain a completely stopped state. This realizes a smooth deceleration before the apparatus stops.

However, since torque is weak in the short brake control, sufficient deceleration may not be obtained from the deceleration by the short brakes. To deal with such a case, in this embodiment, the deceleration control device (CPU 15 in this embodiment) carries out the deceleration control by driving the switching elements Q1-Q4 to feed a motor drive current in the opposite direction to the direction of rotation of the drive motors at the time of traveling drive. In this case, after the deceleration control which feeds the motor drive current in the opposite direction to the direction of rotation of the drive motors at the time of traveling drive, the brakes (electromagnetic brakes in this embodiment) are driven to attain a completely stopped state. Strong torque occurs to the drive motors by feeding the motor drive current in the opposite direction to the direction of rotation of the drive motors at the time of traveling drive, to place the drive motors in a strong deceleration state. This realizes a smooth deceleration before the apparatus stops.

In this embodiment, the short brake control and braking current control are carried out continuously. For example, when traveling at a relatively high speed, strong deceleration may be carried out using the braking current control. When the speed has fallen to some level, deceleration may be carried out using the short brakes. It is therefore preferable, as shown in FIG. 5, to carry out the short brake control (see e in FIG. 5) after the braking current control (see c in FIG. 5).

In particular, it is preferred in this embodiment that the duty ratio altering device (duty ratio altering circuit 18B in this embodiment) alters the duty ratios by determining pulse widths proportional to the rotating speeds of the drive motors detected by the rotating speed detecting device (encoders). Since the pulse widths, and thus the duty ratios, are altered in proportion to the rotating speeds of the drive motors detected by the rotating speed detecting device (encoders), a still smoother deceleration is realized. The pulse widths are determined using, for example, equation (1) noted hereinbefore.

This invention is not limited to the foregoing embodiment, but may be modified as follows:

(1) In the foregoing embodiment, the deceleration control device is the CPU, but may be a circuit construction like the pulse generating circuit or the duty ratio altering circuit. The pulse generating device and the duty ratio altering device are circuit constructions such as the pulse generating circuit and the duty ratio altering circuit, but may be a CPU. Or the deceleration control device, the pulse generating device and the duty ratio altering device may be formed of a programmable device (eg FPGA: Field Programmable Gate Array) with a changeable hardware circuit (eg logic circuit) combining a CPU and a circuit construction.

(2) In the foregoing embodiment, the brakes are electromagnetic brakes represented by disk brakes, for example. However, there is no limitation to anything that has a braking function, exemplified by mechanical brakes (latching brakes) which mechanically lock wheels, tires or motors.

Figure 6:
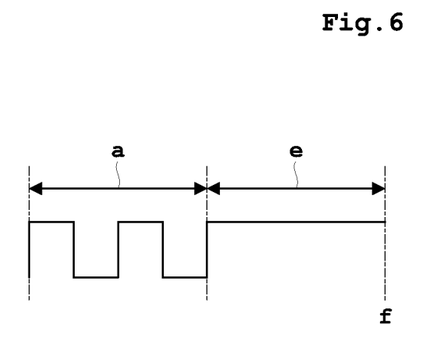
FIG. 6 is a timing chart of a switching pulse signal according to a modification.
Figure 7:
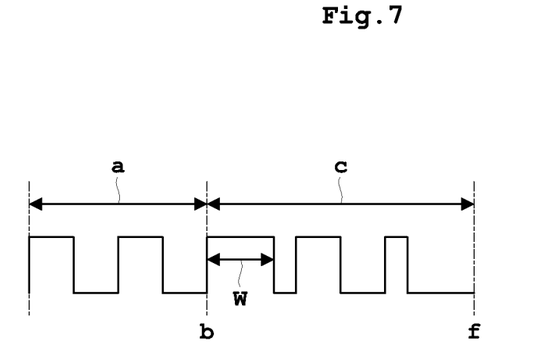
FIG. 7 is a timing chart of a switching pulse signal according to a modification.

(3) In the foregoing embodiment, the short brake control and braking current control are carried out continuously. However, as shown in FIG. 6, after only the short brake control is carried out (see e in FIG. 6), the brakes may be driven at time f in FIG. 6. As shown in FIG. 7, only the braking current control is carried out (see c in FIG. 7), the brakes may be driven at time f in FIG. 7. The (length of) time for performing the short brake control (see e in FIG. 6) may be the predetermined time (eg about 0.5 sec.) noted hereinbefore, or may be a time until detection of the speed of the apparatus having fallen sufficiently (eg to 1 km/h or less). Since the time for performing the short brake control and braking current control in FIGS. 5-7, including FIG. 5, is not very long which is about less than 1 second, the distance (braking distance) the apparatus moves by inertia is not long, even compared with the time of applying the electromagnetic brakes immediately as in the prior art. There is therefore little chance of contacting surrounding obstacles even if the electromagnetic brakes are driven after the deceleration control.

(4) In the foregoing embodiment, the braking current control involves alteration of the duty ratio as shown in FIG. 5. However, the duty ratio may be fixed.

Figure 8:
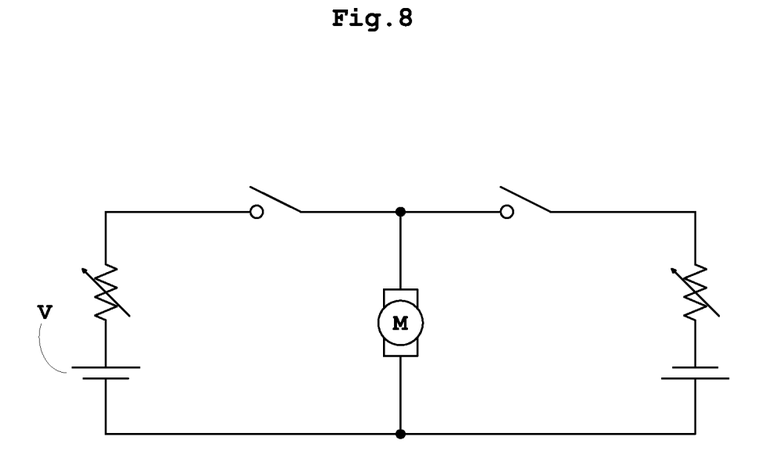
FIG. 8 is a circuit diagram showing a driving circuit according to a modification.

(5) In the foregoing embodiment, the driving circuit is the motor drive circuit 19 in form of the bridge circuit shown in FIG. 4. There is no limitation as long as it is a driving circuit, as exemplified by a circuit as shown in FIG. 8.

REFERENCE SIGNS LIST

1 . . . X-ray apparatus for round visit
2 . . . X-ray tube
4 . . . movable carriage
7 . . . rear wheels
11 . . . right motor
12 . . . left motor
15 . . . CPU
16 . . . right encoder
17 . . . left encoder
18A . . . pulse generating circuit
18B . . . duty ratio altering circuit
19 . . . motor drive circuit
20 . . . right electromagnetic brake
21 . . . left electromagnetic brake
Q1-Q4 . . . switching elements

The invention claimed is:

1. An X-ray apparatus for round visit comprising:
an X-ray emitting device for emitting X-rays;
a movable carriage having the X-ray emitting device;
a lever handle attached to the movable carriage;
traveling drive wheels for moving the movable carriage;
motors for driving the traveling drive wheels;
a motor control device for controlling the motors based on travel controls detected with the lever handle;
a brake lever attached to the movable carriage;
brakes for stopping the movable carriage by mechanical braking; and
a brake control device for controlling the brakes based on a brake operation detected with the brake lever, wherein
the brake control device includes a deceleration control device for carrying out deceleration control of the movable carriage when a brake operation is carried out at the brake lever; and
the brake control device is arranged to stop the movable carriage by driving the brakes after the movable carriage is decelerated by the deceleration control.

2. The X-ray apparatus for round visit according to claim 1, comprising:
a driving circuit having switching elements;
wherein the deceleration control device carries out the deceleration control by driving the switching elements to short-circuit the driving circuit and apply short brakes.

3. The X-ray apparatus for round visit according to claim 1, comprising:
a driving circuit having switching elements;
wherein the deceleration control device carries out the deceleration control by driving the switching elements to feed a motor drive current in an opposite direction to a direction of rotation of the motors at a time of traveling drive.

4. The X-ray apparatus for round visit according to claim 1, comprising:
a driving circuit having switching elements;
wherein the deceleration control device continuously carries out a short brake control as the deceleration control by driving the switching elements to short-circuit the driving circuit and apply short brakes, and a braking current control as the deceleration control by driving the switching elements to feed a motor drive current in an opposite direction to a direction of rotation of the motors at a time of traveling drive.

5. The X-ray apparatus for round visit according to claim 4, wherein the deceleration control device carries out the short brake control after the braking current control.

6. The X-ray apparatus for round visit according to claim 3, comprising:
a pulse generating device for generating pulses, and carrying out ON/OFF control of the switching elements by supplying the pulses to the switching elements; and
a duty ratio altering device for altering duty ratios which are pulse widths divided by pulse periods of the pulses generated by the pulse generating device;
wherein the deceleration control device carries out the deceleration control through the ON/OFF control of the switching elements, while the duty ratio altering device alters the duty ratios.

7. The X-ray apparatus for round visit according to claim 6, comprising:
a rotating speed detecting device for detecting rotating speeds of the motors;
wherein the duty ratio altering device alters the duty ratios by determining pulse widths proportional to the rotating speeds of the motors detected by the rotating speed detecting device.

8. The X-ray apparatus for round visit according to claim 7, wherein the pulse widths are determined from $$W = \alpha \times R / R\text{max}$$

where W represents the pulse widths, $\alpha$ represents a deceleration constant, R represents the rotating speeds of the motors, and Rmax represents a maximum rotating speed of the motors.

9. The X-ray apparatus for round visit according to claim 4, comprising:
a pulse generating device for generating pulses, and carrying out ON/OFF control of the switching elements by supplying the pulses to the switching elements; and
a duty ratio altering device for altering duty ratios which are pulse widths divided by pulse periods of the pulses generated by the pulse generating device;
wherein the deceleration control device carries out the deceleration control through the ON/OFF control of the switching elements, while the duty ratio altering device alters the duty ratios.

10. The X-ray apparatus for round visit according to claim 9, comprising:
a rotating speed detecting device for detecting rotating speeds of the motors;
wherein the duty ratio altering device alters the duty ratios by determining pulse widths proportional to the rotating speeds of the motors detected by the rotating speed detecting device.

11. The X-ray apparatus for round visit according to claim 10, wherein the pulse widths are determined from $$W = \alpha \times R / R\text{max}$$

where W represents the pulse widths, $\alpha$ represents a deceleration constant, R represents the rotating speeds of the motors, and Rmax represents a maximum rotating speed of the motors.

12. The X-ray apparatus for round visit according to claim 1, wherein the lever handle includes sensors to detect a user's operation of the lever handle.

* * * * *